(12) United States Patent
Eberhard et al.

(10) Patent No.: US 6,901,132 B2
(45) Date of Patent: May 31, 2005

(54) SYSTEM AND METHOD FOR SCANNING AN OBJECT IN TOMOSYNTHESIS APPLICATIONS

(75) Inventors: Jeffrey Eberhard, Albany, NY (US); Abdulrahman Al-Khalidy, Clifton Park, NY (US)

(73) Assignee: General Electric Company, Niskayuna, NY (US)

( * ) Notice: Subject to any disclaimer, the term of this patent is extended or adjusted under 35 U.S.C. 154(b) by 49 days.

(21) Appl. No.: 10/607,317

(22) Filed: Jun. 26, 2003

(65) Prior Publication Data

US 2004/0264635 A1 Dec. 30, 2004

(51) Int. Cl.$^7$ ................................................ A61B 6/03
(52) U.S. Cl. ........................................ 378/23; 378/22
(58) Field of Search ................ 378/4, 8, 15, 19, 378/21, 22, 23

(56) References Cited

U.S. PATENT DOCUMENTS

| | | | |
|---|---|---|---|
| 4,008,400 A | 2/1977 | Brunnett et al. | 250/445 |
| 5,187,659 A | 2/1993 | Eberhard et al. | 364/413.15 |

OTHER PUBLICATIONS

D.G. Grant, et al, "Tomosynthesis: A three–dimensional radiographic imaging technique." IEEE Trans on Biomedical Engineering, vol. BME–19, No. 1, Jan. 1972. pp 20–28.

J.T.Dobbins, et al, "Tomosynthesis for improved pulmonary nodule detection." Radiology/RSNA abstract No. 604, p. 280, vol. 290(P).

*Primary Examiner*—David V Bruce
(74) *Attorney, Agent, or Firm*—Fletcher Yoder

(57) ABSTRACT

A tomosynthesis system for scanning a region in an object comprises a radiation source configured to traverse in a plurality of positions yielding a plurality of scanning directions. Each of the plurality of positions corresponds to a respective scanning direction. Further, the plurality of scanning directions comprise at least a scanning direction along a first axis and a direction along a second axis, the second axis being transverse to the first axis.

51 Claims, 5 Drawing Sheets

SYSTEM AND METHOD FOR SCANNING AN OBJECT IN TOMOSYNTHESIS APPLICATIONS

BACKGROUND OF THE INVENTION

The present invention relates generally to the field of imaging, and more specifically to the field of tomosynthesis. In particular, the invention relates to tomosynthesis systems and methods employing new scanning trajectories for an x-ray source and image acquisition points for a detector to yield an improved image of an object.

Tomography is well known for both industrial and medical applications. Conventional tomography is based on a relative motion of the x-ray source, the detector and the object. Typically, the x-ray source and the detector are either moved synchronously on circles or are simply translated in opposite directions. Due to that correlated motion, the location of the projected images of points within the object moves also. Only points from a particular slice, typically called a focal slice, will be projected always at the same location onto the detector and therefore imaged sharply. Object structures above and below the focal slice will be permanently projected at different locations. Because of that, they aren't imaged sharply and will be superimposed as a background intensity to the focal slice. This principle of creating a 3D image with one slice in focus (focal slice) using a discrete number of projections is called tomosynthesis.

Tomosynthesis systems for medical applications, typically use an x-ray source for producing a fan or cone-shaped x-ray beam that is collimated and passes through the patient to then be detected by a set of detector elements. The detector elements produce a signal based on the attenuation of the x-ray beams. The signals may be processed to produce a radiographic projection. The source, the patient, or the detector are then moved relative to one another for the next exposure, typically by moving the x-ray source, so that each projection is acquired at a different angle.

By using reconstruction techniques, such as filtered backprojection, the set of acquired projections may then be reconstructed to produce diagnostically useful three-dimensional images. Because the three-dimensional information is obtained digitally during tomosynthesis, the image can be reconstructed in whatever viewing plane the operator selects. Typically, a set of slices representative of some volume of interest of the imaged object is reconstructed, where each slice is a reconstructed image representative of structures in a plane that is parallel to the detector plane, and each slice corresponds to a different distance of the plane from the detector plane.

In addition, because tomosynthesis reconstructs three-dimensional data from projections, it provides a fast and cost-effective technique for removing superimposed anatomic structures and for enhancing contrast in in-focus planes as compared to the use of a single x-ray radiograph. Further, because the tomosynthesis data consists of relatively few projection radiographs that are acquired quickly, often in a single sweep of the x-ray source over the patient, the total x-ray dose received by the patient is comparable to the dose of a single conventional x-ray exposure and is typically significantly less than the dose received from a computed tomography (CT) examination. In addition, the resolution of the detector employed in tomosynthesis is typically greater than the resolution of detectors used in CT examinations. These qualities make tomosynthesis useful for such radiological tasks as detecting pulmonary nodules or other difficult to image pathologies.

Though tomosynthesis provides these considerable benefits, the techniques associated with tomosynthesis also have disadvantages.

Reconstructed data sets in tomosynthesis often exhibit a blurring of structures in the direction of the projections that were used to acquire the tomosynthesis data. This is expressed in a poor depth resolution of the 3D reconstruction or depth blurring. These artifacts associated with an imaged structure will vary depending on, the orientation of the structure with respect to the acquisition geometry. For example, a linear structure which is aligned with the linear motion of a linear x-ray tomosynthesis system, will appear blurred throughout the depth of the volume of interest, whereas such a structure will be blurred much less by the circular motion of a circular x-ray tomosynthesis system. The blurring of structures may create undesirable image artifacts and inhibit the separation of structures located at different heights in the reconstruction of the imaged volume.

Therefore there exists a need to adapt the current tomosynthesis systems to provide for new scanning trajectories and image acquisition points to address the depth blurring of the imaged object.

BRIEF DESCRIPTION OF THE INVENTION

A tomosynthesis system for scanning a region in an object comprises a radiation source configured to traverse in a plurality of positions yielding a plurality of scanning directions. Each of the plurality of positions corresponds to a respective scanning direction. Further, the plurality of scanning directions comprise at least a scanning direction along a first axis and a direction along a second axis, the second axis being transverse to the first axis.

A method for scanning a region in an object using a tomosynthesis system comprises scanning the region in the object along a first axis and along a second axis, the second axis being transverse to the first axis. Further, the scanning comprises traversing a radiation source in a plurality of positions, each of the plurality of positions corresponding to a respective scanning direction. The method also comprises acquiring a plurality of projection images of the region in the object by using a detector disposed at a predetermined distance from the object.

BRIEF DESCRIPTION OF THE DRAWINGS

The foregoing and other advantages and features of the invention will become apparent upon reading the following detailed description and upon reference to the drawings in which.

DETAILED DESCRIPTION OF SPECIFIC EMBODIMENTS

Figure 1:
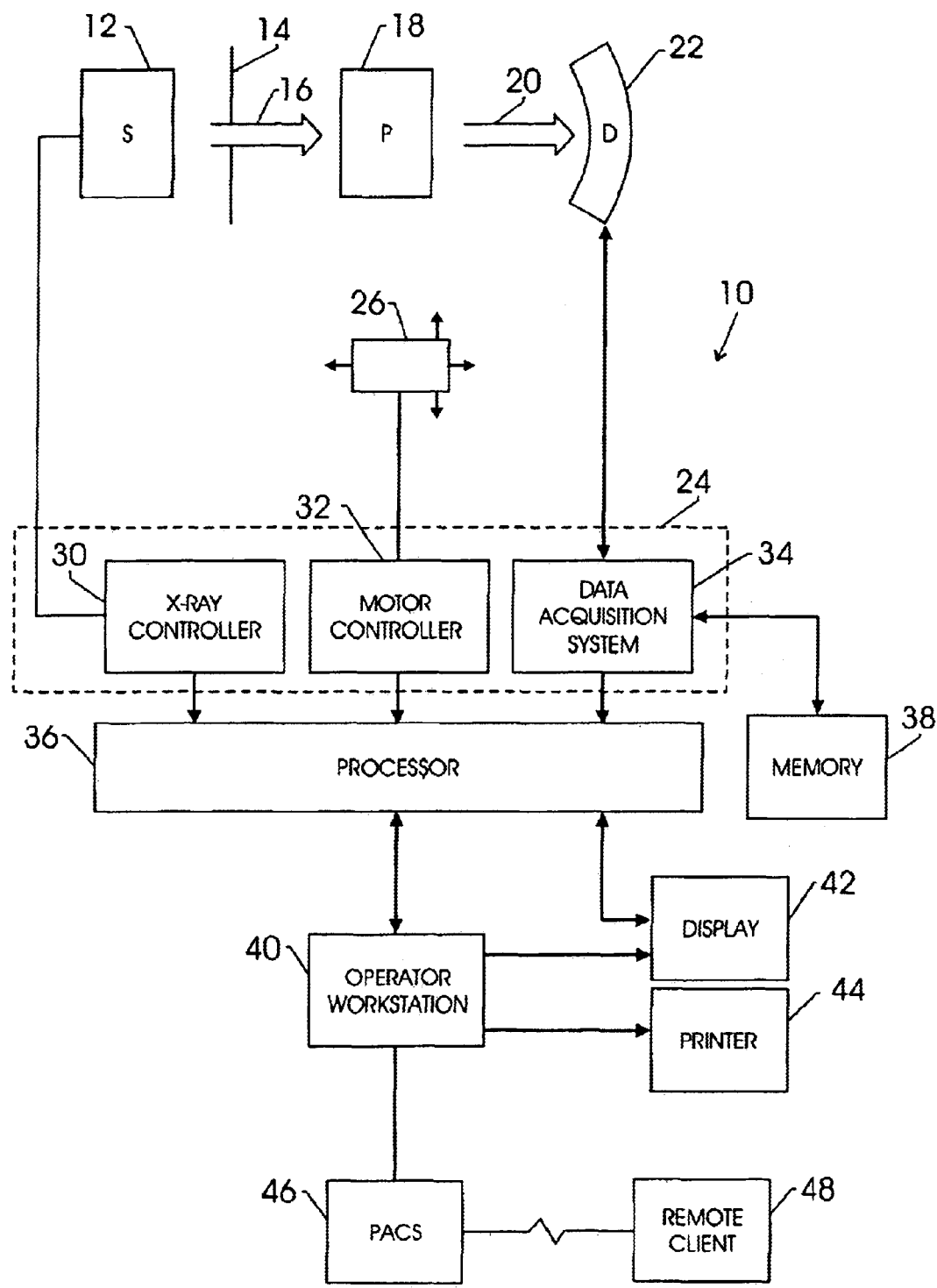
FIG. 1 is a diagrammatical view of an exemplary imaging system in the form of a tomosynthesis system for scanning an object in accordance with aspects of the present technique.

FIG. 1 illustrates diagrammatically an imaging system 10 which may be used for acquiring and processing image data. In the illustrated embodiment, the system 10 is a tomosynthesis system designed both to acquire original image data, and to process the image data for display and analysis in accordance with the present technique. In the embodiment illustrated in FIG. 1, the imaging system 10 includes a source 12 of radiation which is typically x-ray radiation in tomosynthesis, the source 12 is freely movable generally within a plane. In this exemplary embodiment, the x-ray radiation source 12 typically includes an x-ray tube and associated support and filtering components.

A stream of radiation 16 is emitted by the source 12 and impinges an object 18, for example, a patient in medical applications. A portion of the radiation 20 passes through or around the object and impacts a detector array, represented generally at reference numeral 22. Detector elements of the array produce electrical signals that represent the intensity of the incident x-ray beam. These signals are acquired and processed to reconstruct an image of the features within the object. A collimator 14 may define the size and shape of the x-ray beam 16 that emerges from the x-ray source 12.

Source 12 is controlled by a system controller 24 which furnishes both power and control signals for tomosynthesis examination sequences, including positioning of the source 12 relative to the object 18 and the detector 22. Moreover, detector 22 is coupled to the system controller 24, which commands acquisition of the signals generated in the detector 22. The system controller 24 may also execute various signal processing and filtration functions, such as for initial adjustment of dynamic ranges, interleaving of digital image data, and so forth. In general, system controller 24 commands operation of the imaging system to execute examination protocols and to process acquired data. In the present context, system controller 24 also includes signal processing circuitry, typically based upon a general purpose or application-specific digital computer, associated memory circuitry for storing programs and routines executed by the computer, as well as configuration parameters and image data, interface circuits, and so forth.

In the embodiment illustrated in FIG. 1, system controller 24 is coupled to a positional subsystem 26 which positions the x-ray source 12 relative to the object 18 and the detector 22. In alternative embodiments the positional subsystem 26 may move the detector 22 or even the object 18 instead of the source 12 or together with the source 12. In yet another embodiment, more than one component may be movable, controlled by positional subsystem 26. Thus, radiographic projections may be obtained at various angles through the object 18 by changing the relative positions of the source 12, the object 18, and the detector 22 via the positional subsystem 26 according to various embodiments illustrated hereinbelow in detail.

Additionally, as will be appreciated by those skilled in the art, the source of radiation may be controlled by an x-ray controller 30 disposed within the system controller 24. Particularly, the x-ray controller 30 is configured to provide power and timing signals to the x-ray source 12. A motor controller 32 may be utilized to control the movement of the positional subsystem 26.

Further, the system controller 24 is also illustrated comprising a data acquisition system 34. The detector 22 is typically coupled to the system controller 24, and more particularly to the data acquisition system 34. The data acquisition system 34 receives data collected by readout electronics of the detector 22. The data acquisition system 34 typically receives sampled analog signals from the detector 22 and converts the data to digital signals for subsequent processing by a computer 36.

The computer 36 is typically coupled to the system controller 24. The data collected by the data acquisition system 34 may be transmitted to the computer 36 and moreover, to a memory 38. It should be understood that any type of memory adapted to store a large amount of data may be utilized by such an exemplary system 10. Also the computer 36 is configured to receive commands and scanning parameters from an operator via an operator workstation 40, typically equipped with a keyboard and other input devices. An operator may control the system 10 via the input devices. Thus, the operator may observe the reconstructed image and other data relevant to the system from computer 36, initiate imaging, and so forth.

A display 42 coupled to the operator workstation 40 may be utilized to observe the reconstructed image and to control imaging. Additionally, the image may also be printed on to a printer 44 which may be coupled to the computer 36 and the operator workstation 40. Further, the operator workstation 40 may also be coupled to a picture archiving and communications system (PACS) 46. It should be noted that PACS 46 may be coupled to a remote system 48, radiology department information system (RIS), hospital information system (HIS) or to an internal or external network, so that others at different locations may gain access to the image and to the image data.

It should be further noted that the computer 36 and operator workstation 46 may be coupled to other output devices which may include standard or special purpose computer monitors and associated processing circuitry. One or more operator workstations 40 may be further linked in the system for outputting system parameters, requesting examinations, viewing images, and so forth. In general, displays, printers, workstations, and similar devices supplied within the system may be local to the data acquisition components, or may be remote from these components, such as elsewhere within an institution or hospital, or in an entirely different location, linked to the image acquisition system via one or more configurable networks, such as the Internet, virtual private networks, and so forth.

Figure 2:
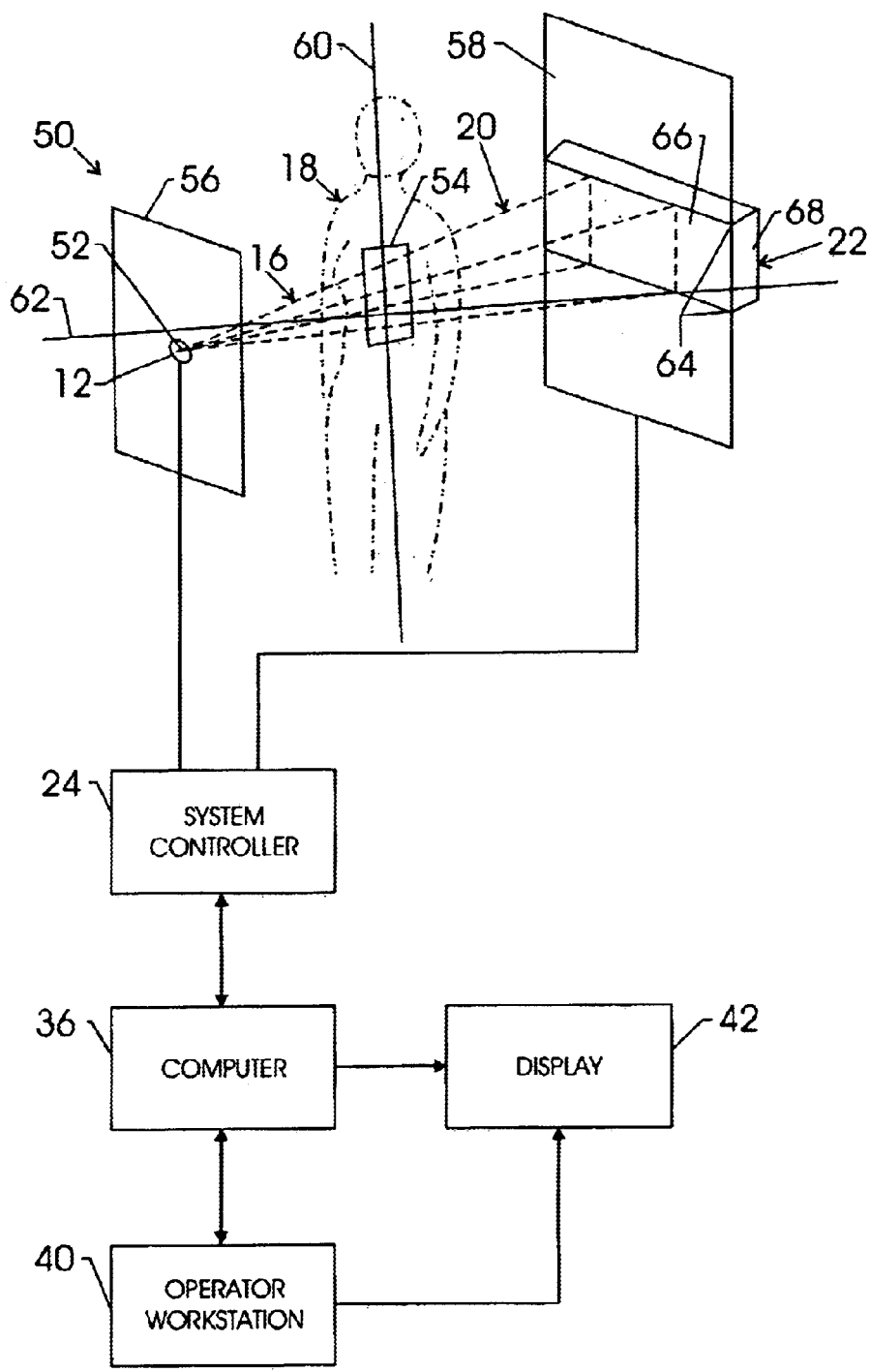
FIG. 2 is a diagrammatical view of a physical implementation of the tomosynthesis system of FIG. 1.

Referring generally to FIG. 2, an exemplary imaging system utilized in a present embodiment may be a tomosynthesis imaging system 50. In an arrangement similar to that described above, the tomosynthesis imaging system 50 is illustrated with a source 12 and a detector 22 between which an object, illustrated as a patient 18 may be disposed. The source of radiation 12 typically includes an x-ray tube which emits x-ray radiation from a focal point 52. The stream of radiation is directed towards a particular region 54 of the patient 18. It should be noted that the particular region 54 of the patient 18 is typically chosen by an operator so that the most useful scan of a region may be made.

In a typical operation, x-ray source 12 is positioned at a predetermined distance above the patient 18 and projects an x-ray beam from the focal point 52 and toward detector array 22. The detector 22 is disposed in a spaced apart relationship with respect to the source 12 and at a predetermined distance from the patient 18. The detector 22 is generally formed by a plurality of detector elements, generally corresponding to pixels, which sense the x-rays that pass through and around a object of interest 54, such as particular body parts, for instance the chest, lungs and so on. In one embodiment, the detector 22 consists of a 2,048×2,048 rectangular array of elements which correspond to a pixel size of 200 μm×200 μm, though other configurations and sizes of both detector 22 and pixel are of course possible. Each detector element produces an electrical signal that represents the intensity of the x-ray beam at the position of the element at the time the beam strikes the detector. Furthermore, the source 12 may be moved generally within a first plane 56, which is substantially parallel to the second plane 58, which is a plane of the detector 22, so that a plurality of radiographic views from different view angles may be collected by the computer 36. The movement of the x-ray source is described in detail with reference to the discussion of FIG. 4, hereinbelow. In one embodiment the distance between the source 12 and the detector 22 is approximately 180 cm and the total range of motion of the source 12 is between 31.5 cm and 131 cm, which translates to ±5° to ±20° where 0° is a centered position. In this embodiment, typically at least 11 projections are acquired, covering the full angular range.

The computer 36 is typically used to control the entire tomosynthesis system 50. The main computer that controls the operation of the system may be adapted to control features enabled by the system controller 24. Further, the operator workstation 40 is coupled to the computer 36 as well as to a display, so that the reconstructed image may be viewed.

As the x-ray source 12 is moved generally within plane 56, the detector 22 collects data of the attenuated x-ray beams. Data collected from the detector 22 then typically undergo pre-processing and calibration to condition the data to represent the line integrals of the attenuation coefficients of the scanned objects. The processed data, commonly called projections, are then typically backprojected to formulate an image of the scanned area. In tomosynthesis, a limited number of projections are acquired, typically thirty or less, each at a different angle relative to the object and detector. Reconstruction algorithms are typically employed to perform the reconstruction on this data to reproduce the initial images.

Once reconstructed, the image produced by the system of FIGS. 1 and 2 reveals the three-dimensional relationship of internal features of the patient 18. The image may be displayed to show these features and their three-dimensional relationships. Though the reconstructed image may comprise a single reconstructed slice representative of structures at the corresponding location within the imaged volume, more than one slice is typical.

Figure 3:
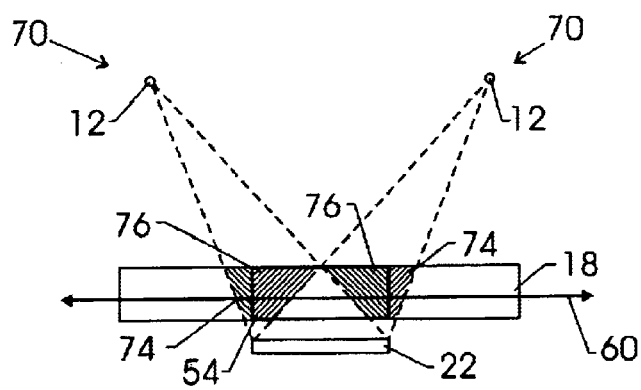
FIG. 3 is a top view of a conventional tomosynthesis system and associated problems in the same.

Referring now to FIG. 3, which illustrates a top view of a typical linear tomosynthesis system and the associated problem with it. Typically, the source 12 is moved linearly in a plane above the patient 18, to image the region 54, the projection images being captured by a fixed detector 22. The source 12 moves along the first axis 60, which is the long body axis of the patient 18 and during this motion it images the extraneous region depicted generally by reference numeral 74 and excludes a part of the region 54, depicted generally by reference numeral 76. Thus in these conventional systems, data from outside (above and below) the region 54 will be contained in the projections and hence in the reconstructions, injecting inconsistency into the reconstruction problem and degrading image quality.

Figure 4:
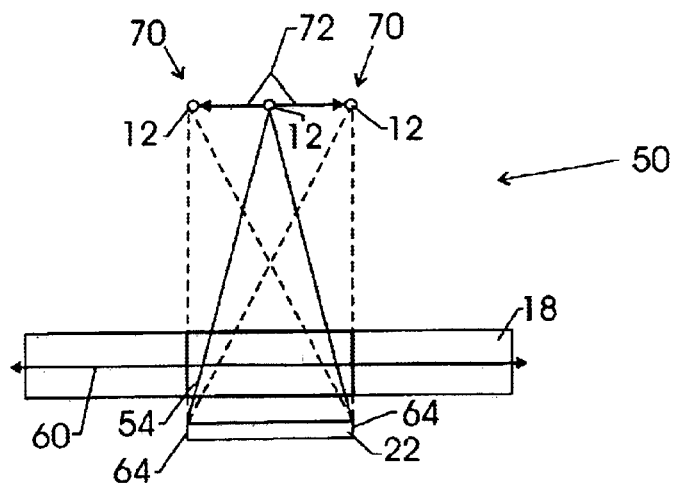
FIG. 4 is a top view of an embodiment of the present techniques to solve the problem illustrated in FIG. 3.
Figure 5:
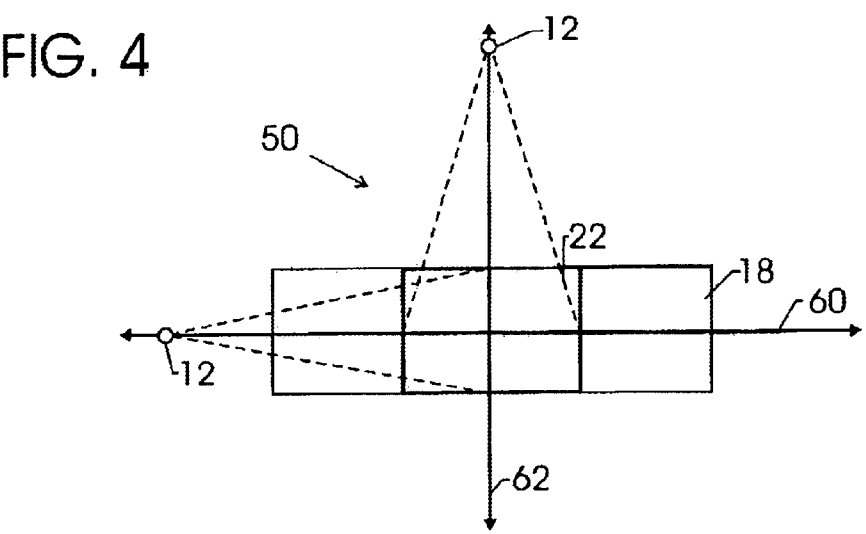
FIG. 5 is a top view of another embodiment of the present technique illustrating the movement of the x-ray source along the long axis of the patient and transverse to the long axis.

FIG. 4 and FIG. 5 illustrate different embodiments to address the problem depicted in FIG. 3. Referring to FIG. 4, it illustrates a top of view of tomosynthesis system 50 for scanning a region 54 in a patient 18. The system 50 comprises a radiation source 12 configured to traverse in a plurality of positions 70, yielding a plurality of scanning directions 72. In this configuration, each of the plurality of positions corresponds to a respective scanning direction. In an exemplary embodiment, at least one of the plurality of positions 70 is defined by an edge 64 of the detector 22 in the direction along the first axis 60 i.e. the long body axis. In this configuration, since the x-ray source 12 moves till the edge 64 of the detector 22, it overcomes the problem shown in FIG. 3, of including an extraneous region i.e. the overlaying tissues of the region 54 during the scanning process. In another exemplary embodiment, at least two of the plurality of positions 70, are defined by two edges 64 of the detector 22.

Further, in yet another exemplary embodiment as shown in FIG. 5, the plurality of scanning directions comprise at least a scanning direction along a first axis 60 i.e. the long body axis and a direction along a second axis 62 i.e. the short body axis, the second axis being transverse to the first axis. In this case, since there is no body tissue beyond the detector in the scanning direction, the problem of tissue from outside the region of interest is, completely eliminated. Thus a two dimensional scanning configuration that scans to the edge of the detector in the body long axis direction depicted by reference numeral 60, and over a longer scan path in the perpendicular direction depicted by reference numeral 62 achieves the benefits of both sharp resolution in the z-direction and elimination of overlying tissue problems from outside the region of interest. An example, where the embodiments will be useful includes but is not limited to, where the region of interest 54 in the patient 18 extends beyond the detector 22 in one direction (e.g. along the axis 60).

In a tomosynthesis system having source to detector distance of 180 cm, scanning an object of 25 cm thickness and of the same lateral dimension as the detector (41 cm×41 cm), located 7 cm in front of the active detector surface, because the object is as wide as the detector, and the x-ray beam is a cone beam diverging from the focal spot, approximately 11% of region on the sides of the object is not covered in any x-ray projection for a scan just along the long body axis (axis 60) in a conventional tomosynthesis system. Using the embodiments described hereinabove, a scan that includes points in the lateral direction at the edges of the detector assures that every imaged element in the reconstruction contains information from at least one x-ray measurement and hence yields a better quality image.

As it would be appreciated by one skilled in the art, the above embodiments yield to several useful scanning configurations and related acquisitions by the detector 22. Illustrated non-limiting examples of these are discussed herein below in reference to FIG. 6 and FIG. 7, several other configurations are possible.

Figure 6:
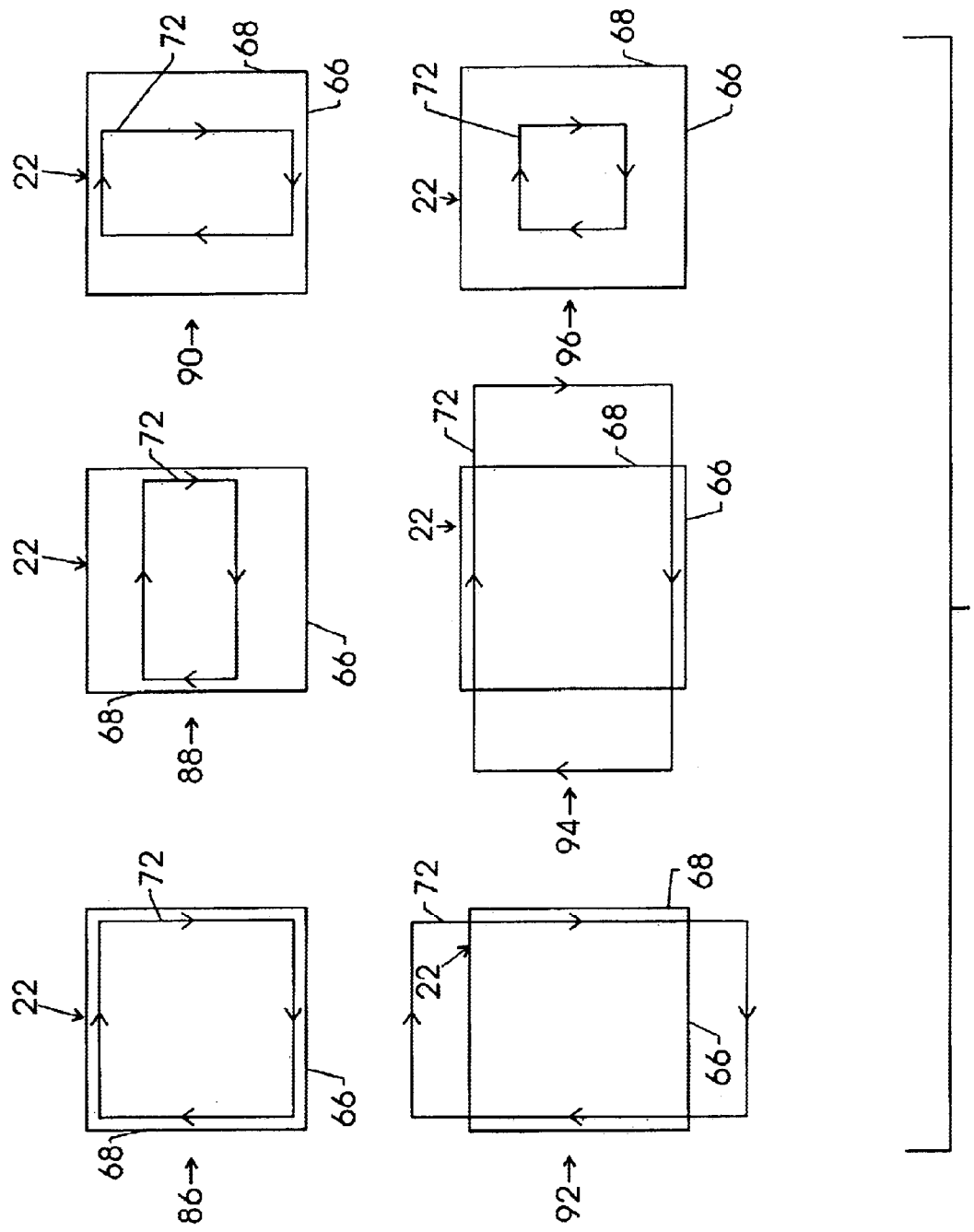
FIG. 6 is a collection of top views of plurality of scanning directions of the x-ray source according to aspects of present technique.

FIG. 6 illustrates an exemplary set of scanning configurations depicted generally by reference numerals 86, 88, 90, 92, 94, and 96, for the various embodiments described hereinabove. In one example, the plurality of scanning directions 72 comprise covering a plurality of areas defined respectively by a plurality of predetermined dimensions of the detector 22. In an exemplary embodiment, the plurality of the predetermined dimensions comprises at least a width 66 and a height 68 of the detector 22. In another example, the plurality of areas comprise at least an area defined by the width 66 and the height 68 of the detector 22. In yet another example, the plurality of areas comprise at least an area defined by the width of the detector and a fraction of the height of the detector. Another example includes at least an area defined by the height of the detector and a fraction of the width of the detector. Yet another example includes at least an area defined by the width of the detector and a multiple of the height of the detector. Another example includes at least an area defined by the height of the detector and a multiple of the width of the detector. Yet another example includes at least an area defined by a portion of the width and a portion of the height of the detector.

Figure 7:
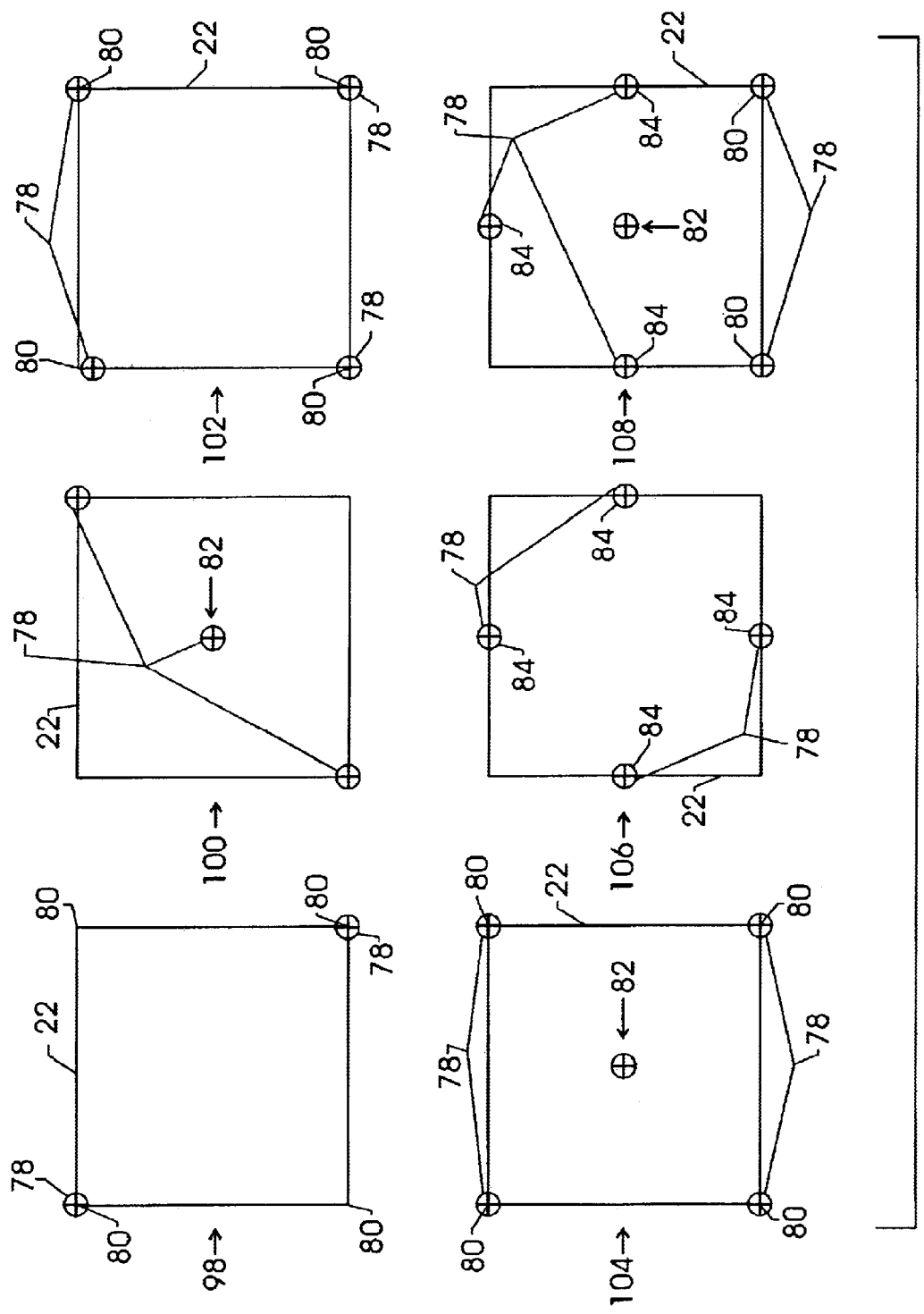
FIG. 7 is a collection of top views of acquisition points by the detector according to aspects of present technique.

FIG. 7 illustrates an exemplary set of plurality of acquisitions points 78, at the detector 22 for acquiring the plurality of projection images, depicted generally by reference numerals 98, 100, 102, 104, 106, and 108. In one example, the plurality of predetermined acquisition points comprise at least two points 78 at two opposite corners 80 of the detector 22. In another example, the plurality of predetermined acquisition points 78, comprise at least two points 78 at two opposite corners 80 of the detector and a point at the center 82 of the detector 22. In yet another example, the plurality of predetermined acquisition points comprise at least four points 78 at four corners 80 of the detector 22. Another example includes at least four points 78 at four corners 80 of the detector and a point at the center 82 of the detector 22. Another example includes at least center points 84 of an each edge of the detector and a point at the center 82 of the detector 22. Yet another example includes at least center points 84 of an each edge of the detector 22. Another example includes at least more than four points along a border of the detector. Yet another example includes at least points at a varying distance defined by the center 82 of the detector and an edge of the detector. In another example, the plurality of predetermined acquisition points 78 comprise at least a plurality of points outside the detector 22, wherein the plurality of points outside the detector correspond to the radiation source positions 70 during the scanning direction along the second axis 62 in a direction transverse to the first axis 60 of the patient 18.

Another exemplary embodiment (not shown) comprises a detector 22, configured to traverse in a plurality of directions in a plane 58, each of the plurality of the directions corresponding respectively to each of the plurality of positions 70 of the radiation source 12. As would be appreciated by those skilled in the art, the scanning configurations and acquisitions described hereinabove are equally applicable to this embodiment wherein the detector is configured to move.

Another aspect of the technique is a method for scanning a region 54 in an object 18 using a tomosynthesis system 50. The method comprises scanning the region 54 in the object 18 along a first axis 60 and along a second axis 62, the second axis being transverse to the first axis. The scanning further comprises traversing a radiation source 12 in a plurality of positions 70, each of the plurality of positions corresponding to a respective scanning direction 72; and acquiring a plurality of projection images of the region in the object by using a detector 22 disposed at a predetermined distance from the object.

Another aspect of the above method includes acquiring a plurality of projection images of the region 54 in the object 18 by using a detector 22 disposed at a predetermined distance from the object. In this aspect, at least one of the plurality of positions is defined by an edge of the detector in the direction along the first axis 60.

As would be appreciated by those skilled in the art the technique also includes the methods for scanning and acquiring images using the various embodiments of the invention described hereinabove.

It would also be appreciated by those skilled in the art that the above embodiments are useful in other imaging modalities as well, non-limiting examples of these include stereotaxy, stereo imaging, for example in mammographic imaging systems. Further besides being useful in medical imaging, the above embodiments have use in industrial imaging as well, for example in testing of flat components such as multilayer printed circuit boards or welding seams in big components.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

What is claimed is:

1. A tomosynthesis system for scanning a region in an object, the system comprising:
a radiation source configured to traverse in a plurality of positions yielding a plurality of scanning directions, wherein each of the plurality of positions corresponds to a respective scanning direction, and wherein the plurality of scanning directions comprise at least a scanning direction along a first axis and a direction along a second axis, wherein the second axis is transverse to the first axis.

2. The system of claim 1, wherein the radiation source projects a radiation beam which impinges the object.

3. The system of claim 1, wherein the radiation source is configured to traverse in the plurality of positions at a predetermined distance above the object.

4. The system of claim 1, further comprising a detector configured to acquire a plurality of projection images of the region in the object from the radiation beam attenuated by the object, wherein the detector is disposed in a spaced apart relationship with respect to the source and at a predetermined distance from the object.

5. The system of claim 3, wherein at least one of the plurality of positions is defined by an edge of the detector in the direction along the first axis.

6. The system of claim 3, wherein at least two of the plurality of positions are defined by two edges of the detector.

7. The system of claim 3, wherein the region in the object extends beyond the detector.

8. The system of claim 3, wherein the plurality of scanning directions comprise covering a plurality of areas defined respectively by a plurality of predetermined dimensions of the detector, wherein the plurality of the predetermined dimensions comprises at least a height and a width of the detector.

9. The system of claim 8, wherein the plurality of areas comprise at least an area defined by the height and the width of the detector.

10. The system of claim 8, wherein the plurality of areas comprise at least an area defined by the width of the detector and a fraction of the height of the detector.

11. The system of claim 8, wherein the plurality of areas comprise at least an area defined by the height of the detector and a fraction of the width of the detector.

12. The system of claim 8, wherein the plurality of areas comprise at least an area defined by the width of the detector and a multiple of the height of the detector.

13. The system of claim 8, wherein the plurality of areas comprise at least an area defined by the height of the detector and a multiple of the width of the detector.

14. The system of claim 8, wherein the plurality of areas comprise at least an area defined by a portion of the width and a portion of the height of the detector.

15. The system of claim 3, wherein the detector is configured to acquire the plurality of projection images at a plurality of predetermined acquisition points at the detector.

16. The system of claim 15, wherein the plurality of predetermined acquisition points comprise at least two points at two opposite corners of the detector.

17. The system of claim 15, wherein the plurality of predetermined acquisition points comprise at least two points at two opposite corners of the detector and a point at the center of the detector.

18. The system of claim 15, wherein the plurality of predetermined acquisition points comprise at least four points at four corners of the detector.

19. The system of claim 15, wherein the plurality of predetermined acquisition points comprise at least four points at four corners of the detector and a point at the center of the detector.

20. The system of claim 15, wherein the plurality of predetermined acquisition points comprise at least center points of a each edge of the detector and a point at the center of the detector.

21. The system of claim 15, wherein the plurality of predetermined acquisition points comprise at least center points of a each edge of the detector.

22. The system of claim 15, wherein the plurality of predetermined acquisition points comprise at least more than four points along a border of the detector.

23. The system of claim 15, wherein the plurality of predetermined acquisition points comprise at least points at a varying distance defined by the center of the detector and an edge of the detector.

24. The system of claim 15, wherein the plurality of predetermined acquisition points comprise at least a plurality of points outside the detector, wherein the plurality of points outside the detector correspond to the radiation source positions during the scanning direction along the second axis.

25. The system of claim 3, wherein the detector is configured to traverse in a plurality of directions, each of the plurality of the directions corresponding respectively to each of the plurality of positions of the radiation source.

26. A tomosynthesis system for scanning a region in an object, the system comprising:
a radiation source configured to traverse in a plurality of positions yielding a plurality of scanning directions, each of the plurality of positions corresponding to a respective scanning direction, wherein the plurality of scanning directions comprise at least a scanning direction along a first axis and a direction along a second axis, wherein the second axis is transverse to the first axis, and wherein the source projects a radiation beam which impinges the object; and
a detector configured to acquire a plurality of projection images of the region in the object from the radiation beam attenuated by the object, wherein said detector is disposed at a predetermined distance from the object, wherein at least one of the plurality of positions is defined by an edge of the detector in the direction along the first axis.

27. The system of claim 26, wherein at least two of the plurality of positions are defined by two edges of the detector.

28. The system of claim 26, wherein the region in the object extends beyond the detector.

29. The system of claim 26, wherein the plurality of scanning directions comprise covering a plurality of areas defined respectively by a plurality of predetermined dimensions of the detector, wherein the plurality of the predetermined dimensions comprises at least a height and a width of the detector.

30. The system of claim 26, wherein the detector is configured to acquire the plurality of projection images at a plurality of predetermined acquisition points at the detector.

31. The system of claim 26, wherein the detector is configured to traverse in a plurality of directions, each of the plurality of the directions corresponding respectively to each of the plurality of positions of the radiation source.

32. A tomosynthesis system for scanning a region in a object, the system comprising:
a radiation source configured to traverse in a plurality of positions yielding a plurality of scanning directions, each of the plurality of positions corresponding to a respective scanning direction, wherein the plurality of scanning directions comprise at least a scanning direction along a first axis and a direction along a second axis, wherein the second axis is transverse to the first axis, and wherein the radiation source projects a radiation beam which impinges the object; and
a detector configured to acquire a plurality of projection images of the region in the object from the radiation beam attenuated by the object, wherein said detector is disposed at a predetermined distance from the object, and wherein the detector is configured to traverse in a plurality of directions, each of the plurality of the directions corresponding respectively to each of the plurality of positions of the source.

33. The system of claim 32, wherein at least one of the plurality of positions is defined by an edge of the detector in the direction along the first axis.

34. The system of claim 32, wherein at least two of the plurality of positions are defined by two edges of the detector.

35. The system of claim 32, wherein the region in the object extends beyond the detector.

36. The system of claim 32, wherein the plurality of scanning directions comprise covering a plurality of areas defined respectively by a plurality of predetermined dimensions of the detector, wherein the plurality of the predetermined dimensions comprises at least a height and a width of the detector.

37. The system of claim 32, wherein the detector is configured to acquire the plurality of projection images at a plurality of predetermined acquisition points at the detector.

38. A tomosynthesis system for scanning a region in a object, the system comprising:
a radiation source configured to traverse in a plurality of positions yielding a plurality of scanning directions, each of the plurality of positions corresponding to a respective scanning direction, wherein the plurality of scanning directions comprise at least a scanning direction along a first axis and a direction along a second axis, wherein the second axis is transverse to the first axis, and wherein the source projects a radiation beam which impinges the object;
a system controller operably coupled to the source;
a detector configured to acquire a plurality of projection images of the region in the object from the radiation beam attenuated by the object, wherein said detector is disposed at a predetermined distance from the object;
a motor controller configured to displace at least one of the source, and the detector;

a data acquisition system operably coupled to the detector configured to receive the plurality of projection images and to form one or more reconstructed slices representative of the region being imaged; and an operator workstation operably coupled to the processing circuit configured to display the one or more reconstructed slices.

39. The system of claim 38, wherein at least one of the plurality of positions is defined by an edge of the detector in the direction along the first axis.

40. The system of claim 38, wherein at least two of the plurality of positions are defined by two edges of the detector.

41. The system of claim 38, wherein the region in the object extends beyond the detector.

42. The system of claim 38, wherein the plurality of scanning directions comprise covering a plurality of areas defined respectively by a plurality of predetermined dimensions of the detector, wherein the plurality of the predetermined dimensions comprises at least a height and a width of the detector.

43. The system of claim 38, wherein the detector is configured to acquire the plurality of projection images at a plurality of predetermined acquisition points at the detector.

44. The system of claim 38, wherein the detector is configured to traverse in a plurality of directions, each of the plurality of the directions corresponding respectively to each of the plurality of positions of the radiation source.

45. A method for scanning a region in an object using a tomosynthesis system, the method comprising:

scanning the region in the object along a first axis and along a second axis, wherein the second axis is transverse to the first axis, and wherein the scanning comprises traversing a radiation source in a plurality of positions, each of the plurality of positions corresponding to a respective scanning direction; and acquiring a plurality of projection images of the region in the object by using a detector disposed at a predetermined distance from the object.

46. The method of claim 45, wherein at least one of the plurality of positions is defined by an edge of the detector in the direction along the first axis.

47. The method of claim 45, wherein at least two of the plurality of positions are defined by two edges of the detector.

48. The method of claim 45, wherein scanning in the plurality of directions comprises covering a plurality of areas defined respectively by a plurality of predetermined dimensions of the detector, wherein the plurality of the predetermined dimensions comprises at least a height and a width of the detector.

49. A method for scanning a region in an object using a tomosynthesis system, the method comprising:

scanning the region in the object along a first axis and along a second axis, wherein the second axis is transverse to the first axis, and wherein the scanning comprises traversing a radiation source in a plurality of positions, each of the plurality of positions corresponding to a respective scanning direction; and acquiring a plurality of projection images of the region in the object by using a detector disposed at a predetermined distance from the object, wherein at least one of the plurality of positions is defined by an edge of the detector in the direction along the first axis.

50. The method of claim 49, wherein at least two of the plurality of positions are defined by two edges of the detector.

51. The method of claim 49, wherein scanning in the plurality of directions comprises covering a plurality of areas defined respectively by a plurality of predetermined dimensions of the detector, wherein the plurality of the predetermined dimensions comprises at least a height and a width of the detector.

* * * * *